(12) United States Patent  
Hanlon-Pena et al.

(10) Patent No.: US 8,016,738 B2  
(45) Date of Patent: Sep. 13, 2011

(54) METHODS AND APPARATUS FOR SELECTING INTRA-AORTIC BALLOON DEFLATION TIMING

(75) Inventors: Patricia Hanlon-Pena, Kingwood, TX (US); Ramzi Hanania, Malden, MA (US); George N. Zantos, Medford, MA (US); Johannes Jacobus Schreuder, Brussels (BE)

(73) Assignee: Arrow International, Inc., Reading, PA (US)

( * ) Notice: Subject to any disclaimer, the term of this patent is extended or adjusted under 35 U.S.C. 154(b) by 941 days.

(21) Appl. No.: 11/633,320

(22) Filed: Dec. 4, 2006

(65) Prior Publication Data

US 2007/0156009 A1 Jul. 5, 2007

Related U.S. Application Data

(60) Provisional application No. 60/756,651, filed on Jan. 5, 2006.

(51) Int. Cl.  
*A61M 29/00* (2006.01)

(52) U.S. Cl. ........................................................ 600/18

(58) Field of Classification Search ............... 600/16–18  
See application file for complete search history.

(56) References Cited

U.S. PATENT DOCUMENTS

| | | | |
|---|---|---|---|
| 4,571,547 A | 2/1986 | Day | |
| 4,692,148 A | 9/1987 | Kantrowitz et al. | |
| 4,809,681 A | 3/1989 | Kantrowitz et al. | |
| 5,169,379 A | 12/1992 | Freed et al. | |
| 5,355,891 A | 10/1994 | Wateridge et al. | |
| 5,913,814 A | 6/1999 | Zantos | |
| 6,258,035 B1 | 7/2001 | Hoeksel et al. | |
| 6,290,641 B1 | 9/2001 | Nigroni et al. | |
| 6,569,103 B2 | 5/2003 | Hoeksel et al. | |
| 6,679,829 B2 * | 1/2004 | Nigroni et al. | 600/18 |
| 6,887,206 B2 | 5/2005 | Hoeksel et al. | |
| 7,090,644 B2 | 8/2006 | Hoeksel et al. | |
| 7,169,109 B2 | 1/2007 | Jansen et al. | |
| 2004/0059183 A1 | 3/2004 | Jansen et al. | |
| 2005/0148812 A1* | 7/2005 | Nigroni et al. | 600/18 |

FOREIGN PATENT DOCUMENTS

EP 0 402 872 12/1990  
WO WO 02/28280 A1 4/2002

OTHER PUBLICATIONS

"PCT Notification Concerning Transmittal of International Preliminary Report on Patentability" dated Dec. 11, 2008 issued by The International Bureau of WIPO in connection with PCT/US2006/046299. (7 pages).

Minich L et al., "Neonatal Piglet Model of Intra-Aortic Balloon Pumping: Improved Efficacy Using Echocardiographic Timing," Annals of Thoracic Surgery, 1998; 66, pp. 1527-1532.

Elghazzawi Z F et al., "Algorithm to Identify Components of Arterial Blood Pressure Signals During Use of an Intra-Aortic Balloon Pump," Journal of Clinical Monitoring, vol. 9, No. 4, Sep. 1993, pp. 297-308.

Pantalos G M et al., "Estimation of Timing Errors for the Intraaortic Balloon Pump Use in Pediatric Patients," ASAIO Journal, 1999, 45(3); pp. 166-171.

(Continued)

*Primary Examiner* — Scott M Getzow  
(74) *Attorney, Agent, or Firm* — Baker & Hostetler LLP

(57) ABSTRACT

The present invention provides methods and apparatus for selecting a deflation timing mode for an intra-aortic balloon (IAB) based on comparison of the time required to deflate the IAB and the time between the ECG R wave and systolic upstroke.

28 Claims, 4 Drawing Sheets

OTHER PUBLICATIONS

Kern M J et al., "Hemodynamic effects of new intra-aortic balloon counterpulsation timing methods in patients: A multicenter evaluation," American Heart Journal, Jun. 1999, vol. 137, No. 6, pp. 1129-1136.

Sakamoto T et al., "New Algorithm of Intra Aortic Balloon Pumping in Patients with Atrial Fibrillation," ASAIO Journal Jan.-Mar. 1995, vol. 41, No. 1, pp. 79-83.

Ohley W J et al., "Intraaortic balloon pump response to arrhythmias: Development and implementation of algorithms," Cardioangiology, May 2002, vol. 51, No. 5, pp. 483-487.

International Searching Authority, "Notification of Transmittal of the International Search Report and The Written Opinion of the International Searching Authority," for International Application No. PCT/US2006/046299, 7 pages.

International Searching Authority, "Notification of Transmittal of the International Search Report and The Written Opinion of the International Searching Authority," for International Application No. PCT/US2006/046299, 7 pages, Dec. 4, 2006.

Communication Supplementary Partial European Search Report dated Feb. 4, 2010 from the European Patent Office in connection with European Patent Application No. 06838963.4, 8 pages.

* cited by examiner

US 8,016,738 B2

METHODS AND APPARATUS FOR SELECTING INTRA-AORTIC BALLOON DEFLATION TIMING

CROSS-REFERENCE TO RELATED APPLICATION

This application claims the benefit of U.S. Provisional Patent Application No. 60/756,651, filed Jan. 5, 2006, the content of which is incorporated by reference.

FIELD OF THE INVENTION

The present invention is directed to methods and apparatus for selecting a deflation timing mode for an intra-aortic balloon (IAB) by an intra-aortic balloon pump (IABP) based on the comparison of the time required to deflate the IAB and the time between a subject's ECG R wave and systolic upstroke of arterial pressure. The invention proactively selects the most appropriate IAB deflation timing mode, which is either initiated by the R wave or is predictive based on information from prior heartbeats.

BACKGROUND OF THE INVENTION

Throughout this application various publications are referred to in parenthesis. Full citations for these references may be found at the end of the specification immediately preceding the claims. The disclosures of these publications are hereby incorporated by reference in their entireties into the subject application to more fully describe the art to which the subject application pertains.

Subjects with poorly functioning hearts can have compromised blood supply to vital organs. The pumping action of the heart and the systemic blood supply can be improved by the use of an intra-aortic balloon pump (IABP) to control an intra-aortic balloon (IAB). IABPs are used in cardiology patients and cardiac surgery patients (Baskett et al., 2002; Mehlhorn et al., 1999).

In each cardiac cycle, the IAB is inflated by means of the pumping device at the end of the ejection phase of the left ventricle of the heart, and is deflated again before the commencement of the following ejection phase. It has been suggested that systemic hemodynamics and myocardial efficiency can be improved by balloon deflation approaching or simultaneous with left ventricular ejection (Kern et al., 1999). For optimal functioning of the IABP, it is important that the IAB be inflated and deflated at the correct times in the cardiac cycle.

Methods and apparatus for controlling the inflation of an IAB have been described, for example, in Sakamoto et al., 1995; U.S. Pat. Nos. 4,692,148, 6,258,035, 6,569,103 and 6,887,206; and U.S. Patent Application Publication Nos. 20040059183 and 20050148812.

Deflation of the IAB can be triggered using the electrocardiogram (ECG) of the subject's heart (e.g., Ohley et al., 2002; U.S. Pat. Nos. 4,692,148, 4,809,681, 6,290,641 and 6,679,829). Typically, the timing of deflation of the IAB is based on the ECG trigger and generally occurs prior to the R Wave. The time for deflating the IAB can be set manually by an experienced person at a fixed time in the cardiac cycle. This manual method is predictive or historical relative to the previous ECG trigger. A disadvantage of this system is that the set deflation time will deviate from the desired deflation time with every acceleration or deceleration of the cardiac cycle, so that the deflation time constantly needs to be adjusted. Furthermore, manually setting the deflation time at a fixed point makes it difficult to properly adjust the deflation time during cardiac arrhythmia, which has unpredictable accelerations or decelerations of the cardiac cycle. Arrhythmia often occurs in subjects who require an IABP. Due to these unpredictable accelerations and decelerations of the cardiac cycle, R wave deflation of the IAB is often used during cardiac arrhythmia.

There is a need for an IABP that evaluates the likely hemodynamic results of different modes of IAB deflation and selects a deflation mode based on that evaluation to improve the efficacy of IABP therapy without the need for manual intervention by a clinician.

SUMMARY OF THE INVENTION

The present invention satisfies this need by providing an improved method for selecting a deflation timing mode for an intra-aortic balloon (IAB) by an intra-aortic balloon pump (IABP). The method of the present invention comprises the steps of: a) determining a pre-ejection period (PEP) time (T1), where T1 is the time between an R wave of a subject's electrocardiogram (ECG) and systolic upstroke of the subject's arterial pressure; b) subtracting PEP time (T1) from an IAB deflation time (T2), where T2 is the time from the issuance of a deflation command until the IAB is deflated; c) comparing T2-T1 to a threshold time, where the threshold time allows the IAB to be at least partially deflated prior to systole; and d) if T2-T1 is less than the threshold time, selecting a mode of deflation of the IAB that is initiated by the R wave of the ECG, and if T2-T1 is greater than or equal to the threshold time, selecting a mode of deflation of the IAB that uses information from prior heartbeats to predict a deflation time, which can result in a deflation time earlier than that of R wave deflation.

The present invention also provides an apparatus for selecting a deflation timing mode for an IAB. The apparatus of the invention comprises a processing unit for: a) determining a pre-ejection period (PEP) time (T1), where T1 is the time between an R wave of a subject's electrocardiogram (ECG) and systolic upstroke of the subject's arterial pressure; b) subtracting (PEP) time (T1) from an IAB deflation time (T2), where T2 is the time from the issuance of a deflation command until the IAB is deflated; and c) comparing T2-T1 to a threshold time, where the threshold time allows the IAB to be at least partially deflated prior to systole; wherein if T2-T1 is less than the threshold time, the processing unit selects a mode of IAB deflation that is initiated by the R wave of the ECG, and if T2-T1 is greater than or equal to the threshold time, the processing unit selects a mode of IAB deflation that uses information from prior heartbeats to predict a deflation time.

The method and apparatus of the present invention advance the state of IABP timing by proactively evaluating multiple parameters to select the most appropriate deflation timing method and trigger mode, thereby reducing the risk of incorrect or inappropriate timing without user intervention and improving the efficacy of IABP therapy. The invention is dynamic in that it continuously measures the current conditions of the subject and updates the IABP trigger and timing decisions as new information becomes available.

Additional objects of the invention will be apparent from the description that follows.

DETAILED DESCRIPTION OF THE INVENTION

Figure 1:
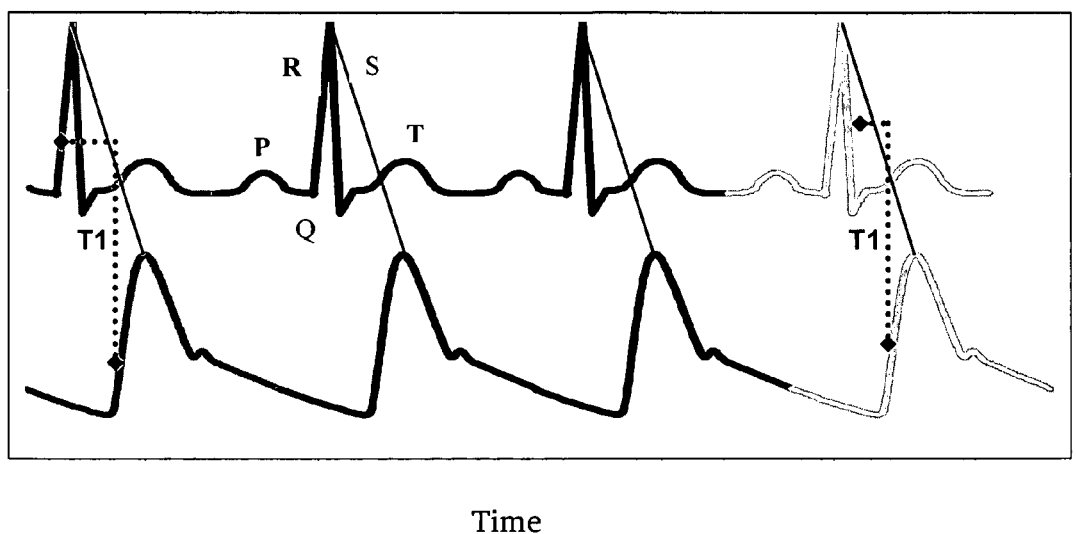
FIG. 1. Illustration of PEP (Pre-ejection period) T1 measurement. PEP is measured from the trigger point detected on the ECG (upper trace) to the point where arterial pressure (lower trace) upstroke is detected. The R-wave of the QRS complex of the ECG is the large peak indicated by arrows and diagonal lines. The P-wave precedes the QRS complex while the T-wave occurs after the QRS complex.

The present invention is directed to methods and apparatus for selecting a deflation timing mode for an intra-aortic balloon (IAB) by an intra-aortic balloon pump (IABP). The invention can be used in subjects with a normal cardiac rhythm. However, the invention is particularly useful in subjects who have a cardiac arrhythmia. The invention may be used in the treatment of human subjects or in veterinary medicine.

The method of the present invention comprises the following steps a)-d).

Step a) involves determining a pre-ejection period (PEP) time (T1), where T1 is the time between an R wave of a subject's electrocardiogram (ECG) and systolic upstroke of the subject's arterial pressure.

Step b) involves subtracting (PEP) time (T1) from an IAB deflation time (T2), where T2 is the time from the issuance of a deflation command until the IAB is deflated. Preferably, as used herein, the IAB is considered deflated when it is 90% to 100% deflated.

Step c) involves comparing T2-T1 to a threshold time, where the threshold time allows the IAB to be at least partially deflated prior to systole. The threshold time can be selected to target a percentage of volume to be removed from the IAB prior to the next systolic upstroke. Preferably, the threshold time that is selected allows the IAB to be about 50% to 70% deflated prior to systole. The residual volume in the IAB represents a potential increase in end diastolic pressure. When the residual volume of the IAB is high, the left ventricle will have to pump against a high pressure, potentially increasing the work of the ventricle. Preferably, the threshold time is 60-90 ms and more preferably 70-80 msec. Most preferably, the threshold time is about 76 msec. The selected threshold value provides confidence that the IAB can be deflated to at least 50% of the specified volume in the amount of time available (PEP). If the threshold value is small, there is a higher degree of confidence that the IAB will be mostly deflated prior to systolic ejection. Conversely, if the threshold value is large, there is little or no confidence that the IAB can be even 50% deflated at the start of systolic ejection. In the case where a high threshold value is used, there is a high likelihood that hemodynamically late deflation will result.

Step d) involves selecting the mode of deflation of the IAB. If T2-T1 is less than the threshold time, a mode of deflation of the IAB is selected that is initiated by the R wave of the ECG. If T2-T1 is greater than or equal to the threshold time, a mode of deflation of the IAB is selected that uses information from prior heartbeats to predict a deflation time. Preferably, the mode of deflation that uses predictive information from prior heartbeats results in a deflation time earlier than that of R wave deflation. The mode of deflation that uses information from prior heartbeats to predict a deflation time can use, for example, the beat-to-beat time from the prior one to, e.g., eight heartbeats. The beat-to-beat time can be averaged. A weighted average can be used where information from more recent heartbeats is weighted more heavily than information from earlier heartbeats.

The invention also provides apparatus for selecting a deflation timing mode for an intra-aortic balloon (IAB) by an intra-aortic balloon pump (IABP), where the apparatus comprises a processing unit for:

a) determining a pre-ejection period (PEP) time (T1), where T1 is the time between an R wave of a subject's electrocardiogram (ECG) and systolic upstroke of the subject's arterial pressure;

b) subtracting (PEP) time (T1) from an IAB deflation time (T2), where T2 is the time from the issuance of a deflation command until the IAB is deflated, preferably 90% to 100% deflated; and c) comparing T2-T1 to a threshold time, where the threshold time allows the IAB to be at least partially deflated prior to systole;

wherein if T2-T1 is less than the threshold time, the processing unit selects a mode of deflation of the IAB that is triggered by the R wave of the ECG, and if T2-T1 is greater than or equal to the threshold time, the processing unit selects a mode of deflation that uses information from prior heartbeats to predict a deflation time, which preferably results in a deflation time earlier than that of R wave deflation.

Preferably, the apparatus also includes inputs from the subject's electrocardiogram (ECG) and from the subject's arterial pressure (AP), inputs for inputting the IAB deflation time (T2) and the threshold time, and a processing unit for detecting cardiac arrhythmia in the subject from the subject's electrocardiogram (ECG) and/or from the subject's arterial pressure. Preferably, the apparatus also includes an output that triggers deflation of the IAB. The apparatus can be incorporated in an intra-aortic balloon pump console system.

The method or processing unit may also calculate values of T2-T1 for periods of several heartbeats, e.g. 20 heartbeats, and then select a trigger mode based on whether T2-T1 is greater than, less than, or equal to the threshold time for the 20 beat period or for each of several, e.g. three consecutive, 20 beat periods.

The method or processing unit can further include determining, during a deflation timing evaluation period, the number of times deflation occurs on an R wave; and if the number of times deflation occurs on the R wave exceeds a threshold value, selecting a mode of deflation that uses information from prior heartbeats to predict a deflation trigger that targets a percentage of volume to be removed from the IAB prior to the next systolic upstroke. The threshold value can be, for example, 14 occurrences of deflation on the R wave during a period of 20 heartbeats.

The method or processing unit can, for example, select a mode of deflation of the IAB that is triggered by the R wave of the ECG if during a deflation timing evaluation period, T2-T1 is less than 76 msec and if the number of occurrences of deflation on the R wave is less than 15 per 20 heartbeats.

The present invention is illustrated in the following Experimental Details section, which is set forth to aid in the understanding of the invention, and should not be construed to limit in any way the scope of the invention as defined in the claims that follow thereafter.

EXPERIMENTAL DETAILS

Introduction

Current IABP systems set deflation timing in one of two ways, predictive or real time. When predictive deflation timing is used, the pump uses information from prior beats (historical average) and targets a percentage of volume that should be removed prior to the next systolic upstroke. The second method initiates deflation on the R-Wave (real time). This method is often used during periods of arrhythmia.

In both of these cases the only stimulus to the timing method is whether an arrhythmia is present; there is no active evaluation to determine if one method or the other is more clinically suited to the current situation. Some pumps actively move deflation timing settings and evaluate the result on end diastolic pressure, looking to achieve the greatest reduction in that pressure. However, they do not proactively evaluate the conditions that determine deflation timing efficacy. They are also only single point evaluations done after the timing is set, rather than being proactive in evaluating and selecting a deflation method that is appropriate to the current patient and pump conditions.

Examples of the Present Invention

In the present invention, deflation timing evaluation is a comparative method that can be implemented, for example, when an arrhythmia is detected by the IABP. The method compares the Pre-ejection period time (T1) to the Balloon deflation speed (T2) in the following equation: T2−T1=Calculated Threshold value.

T2 represents the total time to remove 90 to 100% of the helium from the IAB. T1 represents the time that is available to deflate the IAB when R wave deflation is implemented.

The calculated threshold value or delta value provides confidence that the IAB can be deflated to at least the 50% value in the amount of time available (PEP). If the calculated delta value is small, there is a higher degree of confidence that the IAB will be mostly deflated prior to systolic ejection. Conversely, if the calculated delta value is large, there is little or no confidence that the IAB can be even 50% deflated at the start of systolic ejection. In this case, there is a high likelihood that hemodynamically late deflation will result.

The threshold value represents the limit of the calculated delta value that will meet a minimum of 50% deflation. In fact, the present approach was to be conservative and require closer to 70% IAB deflation prior to systolic ejection. The smaller the threshold value, the higher the amount of helium removal from the IAB prior to the beginning of systolic ejection. This may be due to a long PEP or a faster IAB deflation speed. Conversely, the larger the value, the less time there is for removal of helium from the IAB. This may be due to a shorter PEP or a slower IAB deflation speed.

Based on this information and with the goal of at least 50% of helium removed before the beginning of the systolic ejection, a series of experiments was performed to determine the threshold value.

These experiments tested several different IAB catheters that have different deflation speeds. The effect of deflation timing on the end diastolic pressure was evaluated using different threshold values and different IABs. The criteria for acceptance were that the end diastolic pressure could be slightly higher than the end diastolic pressure, but the systolic upstroke slope must be maintained. Based on this testing it was concluded that a threshold value of 76 msec was an acceptable value under a wide range of conditions.

Simulation Procedures

A series of patient simulators has been used that produce a variety of ECG signals, including various heart rates and rhythms. These signals are used as input for the IABP and for a simulated aorta. The simulated aorta is made of tubing, adjustable compliance chambers, and valves that are driven by ECG signals from physiologic simulators, and produces an arterial pressure similar to that of a patient. The aorta has an opening that allows the IAB catheter to be inserted into it. It also has the ability to change the PEP value, the amplitude and duration of the systolic pulse, and the diastolic pressure level. This allows testing under a variety of conditions that may be seen clinically.

The pressure in the aorta is measured using transducers, either conventional fluid transducers (Wheatstone bridge) or via a Fiber optic pressure sensor. The pressures are connected to the IABP. The IABP data output is connected to a computer that has special diagnostic software to monitor the parameters used and to show the results of the algorithm evaluation.

When the pump is on and assisting, the pressure changes in the simulated aorta are similar to that of a real patient. By varying the input of the ECG and the conditions of the aorta, the performance and decision of the algorithm can be observed.

Examples of Selection of IABP Deflation Mode

When an arrhythmia is detected, the pump begins the deflation timing evaluation period to determine which deflation mode to use.

Deflation timing is moved earlier using 105% of the IAB deflation speed instead of 87%. This results in an accurate measurement of the time period between the ECG R-wave and the arterial pressure upstroke. This period is known as the Pre-ejection period or PEP (FIG. 1). PEP is a critical factor in the effectiveness of IAB deflation timing. This information is recorded as T1.

Figure 2:
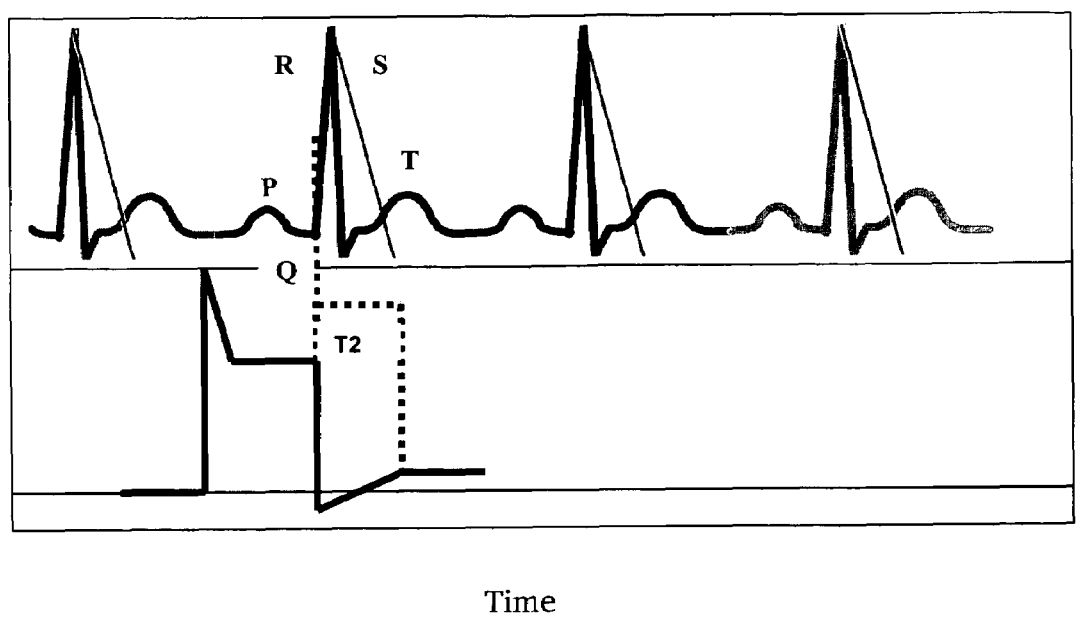
FIG. 2. Illustration of the deflation time T2, which is the time from the start of deflation to the end of deflation. ECG shown on upper trace. When R-wave deflation is used, deflation starts when the trigger point is detected. Deflation ends when the Balloon Pressure Waveform (bottom trace) returns to the baseline. This indicates that at least 90% of the helium has returned to the IABP (pump) from the IAB (Balloon).

The deflation speed of the IABP is measured and saved by software as T2 (FIG. 2).

Since arrhythmia produces an irregular rhythm there is a higher possibility that the deflation point will occur on the R wave. The number of times R-Wave deflation occurs is recorded and saved.

With the information recorded above, the following comparison was performed:

1) The value of T2-T1 was calculated on each beat over a 20 beat period.

2) This value was compared to the threshold value (76 msec) that was derived using clinical information indicating that deflation should be approximately 50% completed at the beginning of systolic ejection. Experiments were performed using different devices under controlled conditions to determine the appropriate threshold value.

3) If the product of T2-T1 for each of 3 consecutive 20 beat segments is <76 msec, R Wave deflation is acceptable and the R wave deflation mode will be selected by the IABP.

4) If the product of T2-T1 for each of 3 consecutive 20 beat segments is ≧76 msec, R Wave deflation is not acceptable and is likely to produce late deflation and the predictive deflation mode will be selected by the IABP.

5) The number of times deflation occurs on the R-Wave during the deflation timing evaluation period is recorded. If the number of "hits" is >14, then the prevailing rhythm is very irregular and the predictive deflation mode will be selected.

The evaluation of this information is updated continuously and the timing method and trigger mode are updated based on current conditions.

Figure 3:
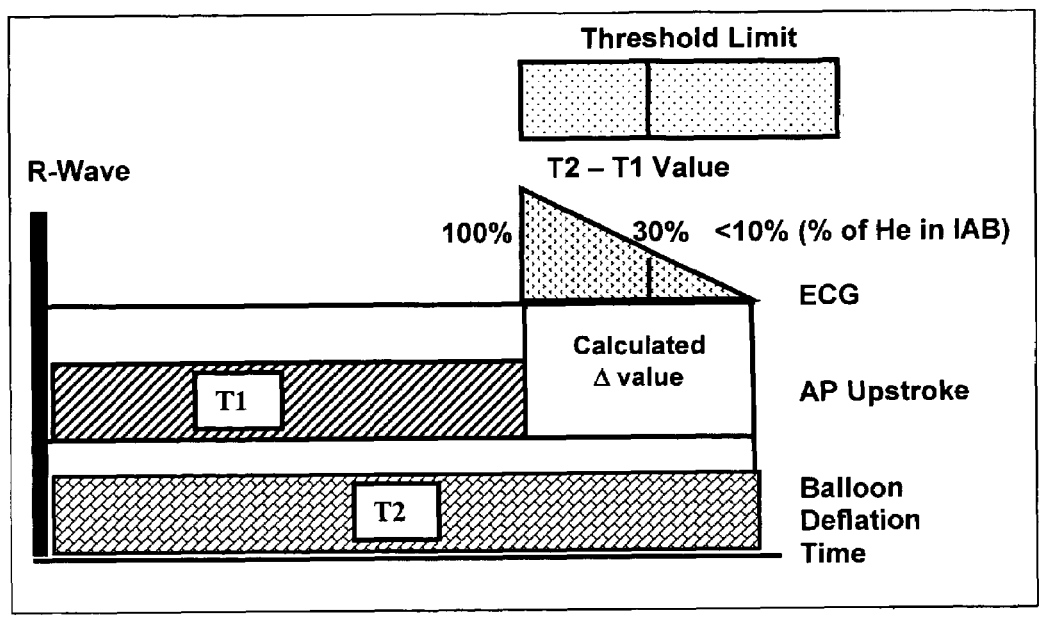
FIG. 3. Schematic of relationship between electrocardiogram (ECG), arterial pressure (AP) and intra-aortic balloon (Balloon) Speed with R-Wave deflation. T2-T1 value calculation is shown. The amount of Helium (He) remaining in the IAB is shown, with 100% to the left side and <10% to the right of the graph. The threshold value is shown above the % of He remaining graph. In the illustration shown in the Figure, the threshold value represents the point where approximately 70% of the He is removed from the IAB; this point is shown on the % of He remaining at 30%.

FIG. 3 illustrates a schematic of the relationship between ECG, AP and Balloon Speed with R-Wave deflation. T2-T1 value calculation is shown.

Figure 4:
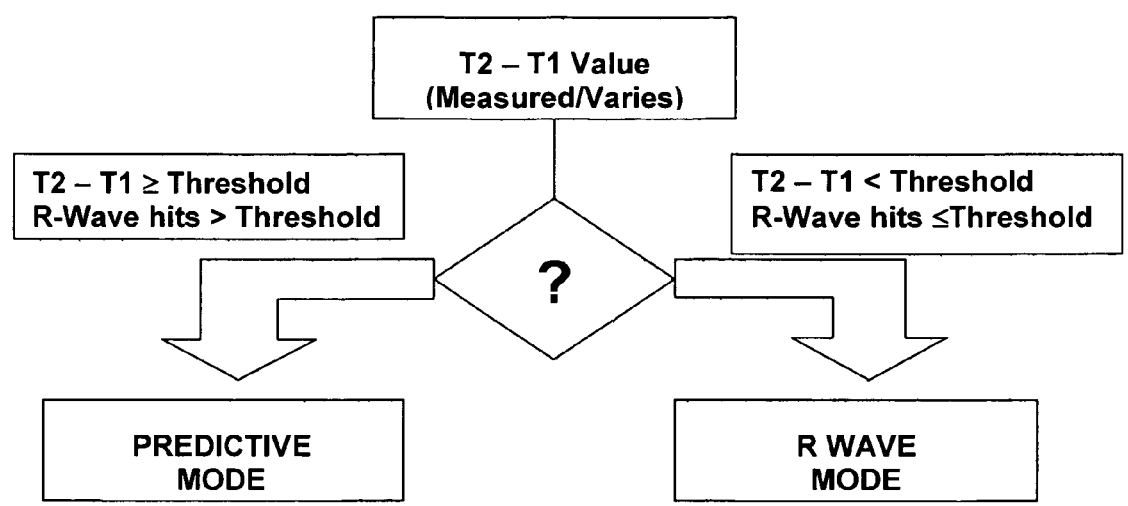
FIG. 4. Schematic of selection of mode of deflation timing.

By comparing the calculated value of T2-T1 to the threshold, one can determine the acceptable method of deflation timing and select the trigger mode that uses it. FIG. 4 shows the schematic of selection of the mode of deflation timing.

The threshold value for T2-T1 was developed by experimenting with the aorta under different conditions as well as mathematical modeling of the IABP system. The goal was to allow a small increase in end diastolic pressure and ensure that the LAB was approximately 70% deflated prior to the next systolic upstroke. Using different IAB catheters and varying the condition in the aorta, an appropriate threshold value was determined to be 76 msec. That means that the IAB deflation time must be at least 76 msec longer than the PEP when R-Wave deflation is used. The IAB could deflate on the R-Wave 14 times or less in 20 beats, approximately 70% of the time. These values were set as the threshold values. The implementation is as follows:

When T2-T1<76 msec and R-Wave hits <15, R-Wave deflation is OK and is selected by the IABP;

In all other cases the pump will select predictive deflation (where deflation can occur prior to the R-Wave).

Using the simulated aorta, the heart rate, cardiac rhythm, balloon speed and PEP values were varied, and the results observed. In all cases, the IABP responded appropriately and did not allow the end diastolic pressure to rise above clinically acceptable levels.

REFERENCES

Baskett R J, Ghali W A, Maitland A, Hirsch G M. The intraaortic balloon pump in cardiac surgery. Ann. Thorac. Surg. 74(4):1276-87, 2002.

Kern, M, Aguirre, F, Caracciolo, E, Bach, R, Donohue, T, Lasorda, D, Ohman, M, Schnitzler, R, King, D, Ohley, W, Grayzel, J. Hemodynamic effects of new intra-aortic balloon counterpulsation timing method in patients: A multicenter evaluation. American Heart Journal 137:1129-6, 1999.

Mehlhorn U, Kroner A, de Vivie E R. 30 years clinical intra-aortic balloon pumping: facts and figures. Thorac. Cardiovasc. Surg. 47 Suppl 2:298-303, 1999.

Ohley, W J, Nigroni, P, Williams, J, Sarras, L, Hamilton, R. Intraaortic balloon pump response to arrhythmias: Development and implementation of algorithms. Cardioangiology 51(5): 483-7, 2002.

Sakamoto, T, Arai, H, Toshiyuki, M, Suzuki, A. A new algorithm of intra aortic balloon pumping in patients with atrial fibrillation. ASAIO Journal 41:79-83, 1995.

U.S. Pat. No. 4,692,148, Intra-aortic balloon pump apparatus and method of using same, Kantrowitz et al., issued Sep. 8, 1987.

U.S. Pat. No. 4,809,681, Electrocardiographic measurement method for controlling an intra-aortic balloon pump, Kantrowitz et al., issued Mar. 7, 1989.

U.S. Pat. No. 6,258,035, Device for determining a characteristic point in the cardiac cycle, Hoeksel et al., issued Jul. 10, 2001.

U.S. Pat. No. 6,290,641, Intra-aortic balloon pump having improved automated electrocardiogram based intra-aortic balloon deflation timing, Nigroni et al., issued Sep. 18, 2001.

U.S. Pat. No. 6,569,103, Device for determining a characteristic point in the cardiac cycle, Hoeksel et al., issued May 27, 2003.

U.S. Pat. No. 6,679,829, Intra-aortic balloon pump having improved automated electrocardiogram based intra-aortic balloon deflation timing, Nigroni et al., issued Jan. 20, 2004.

U.S. Pat. No. 6,887,206, Device for determining a characteristic point in the cardiac cycle, Hoeksel et al., issued May 3, 2005.

U.S. Patent Application Publication No. 2004/0059183, Apparatus for controlling heart assist devices, Jansen et al., published Mar. 25, 2004.

U.S. Patent Application Publication No. 2005/0148812, Timing of intra-aortic balloon pump therapy, Nigroni et al., published Jul. 7, 2005.

What is claimed is:

1. A method of selecting a deflation timing mode for an intra-aortic balloon (IAB) by an intra-aortic balloon pump (IABP), the method comprising:
   a) determining a pre-ejection period (PEP) time (T1), where T1 is the time between an R wave of a subject's electrocardiogram (EGG) and systolic upstroke of the subject's arterial pressure;
   b) subtracting (PEP) time (T1) from an IAB deflation time (T2), where T2 is the time from the issuance of a deflation command until the IAB is deflated;
   c) comparing T2-T1 to a threshold time, where the threshold time allows the IAB to be at least partially deflated prior to systole; and
   d) if T2-T1 is less than the threshold time, selecting a mode of deflation of the IAB that is triggered by the R wave of the EGG, and if T2-T1 is greater than or equal to the threshold time, selecting a mode of deflation of the IAB that uses information from prior heartbeats to predict a deflation time,
   thereby selecting a deflation timing mode for an intra-aortic balloon (IAB) by an intra-aortic balloon pump (IABP).

2. The method of claim 1, wherein the subject has a cardiac arrhythmia.

3. The method of claim 1, wherein the threshold time targets a percentage of volume to be removed from the IAB prior to the next systolic upstroke.

4. The method of claim 3, wherein the threshold time allows the IAB to be about 50% to 70% deflated prior to systole.

5. The method of claim 1, wherein the threshold time is 60-90 msec.

6. The method of claim 1, wherein the threshold time is 70-80 msec.

7. The method of claim 1, wherein the threshold time is about 76 msec.

8. The method of claim 1, wherein the mode of deflation that uses predictive information from prior heartbeats results in a deflation time earlier than that of R wave deflation.

9. The method of claim 1, which further comprises calculating values of T2-T1 for periods of 20 heartbeats, and selecting a trigger mode based on whether T2-T1 is greater than, less than, or equal to the threshold time for each of three consecutive 20 beat periods.

10. The method of claim 1, which further comprises determining, during a deflation timing evaluation period, the number of times deflation occurs on the R wave; and
   if the number of times deflation occurs on the R wave exceeds a threshold value, selecting a mode of deflation that uses information from prior heartbeats to predict a deflation trigger that targets a percentage of volume to be removed from the IAB prior to the next systolic upstroke.

11. The method of claim 10, wherein the threshold value is 14 occurrences of deflation on the R wave during a period of 20 heartbeats.

12. The method of claim 9, which comprises selecting a mode of deflation of the IAB that is triggered by the R wave of the ECG if during a deflation timing evaluation period, T2-T1 is less than 76 msec and if the number of occurrences of deflation on the R wave is less than 15 per 20 heartbeats.

13. An apparatus for selecting a deflation timing mode for an intra-aortic balloon (IAB) by an intra-aortic balloon pump (IABP), the apparatus comprising a processing unit configured programmed for:
   a) determining a pre-ejection period (PEP) time (T1), where T1 is the time between an R wave of a subject's electrocardiogram (ECG) and systolic upstroke of the subject's arterial pressure;
   b) subtracting (PEP) time (T1) from an IAB deflation time (T2), where T2 is the time from the issuance of a deflation command until the IAB is deflated; and
   c) comparing T2-T1 to a threshold time, where the threshold time allows the IAB to be at least partially deflated prior to systole;
   wherein if T2-T1 is less than the threshold time, the processing unit selects a mode of deflation of the IAB that is triggered by the R wave of the ECG, and if T2-T1 is greater than or equal to the threshold time, the processing unit selects a mode of deflation that uses information from prior heartbeats to predict a deflation time.

14. The apparatus of claim 13, wherein the apparatus comprises an input from the subject's electrocardiogram (ECG) to the processing unit.

15. The apparatus of claim 13, wherein the apparatus comprises an input from the subject's arterial pressure to the processing unit.

16. The apparatus of claim 13, wherein the apparatus further comprises a unit for processing the subject's electrocardiogram (ECG) and/or arterial pressure to detect cardiac arrhythmia in the subject.

17. The apparatus of claim 13, wherein the processing unit compares T2-T1 to a threshold time that targets a percentage of volume to be removed from the IAB prior to the next systolic upstroke.

18. The apparatus of claim 17, wherein the processing unit compares T2-T1 to a threshold time that allows the IAB to be about 50% to 70% deflated prior to systole.

19. The apparatus of claim 13, wherein the threshold time is 60-90 msec.

20. The apparatus of claim 13, wherein the threshold time is 70-80 msec.

21. The apparatus of claim 13, wherein the threshold time is about 76 msec.

22. The apparatus of claim 13, wherein the processing unit selects a mode of deflation of the IAB that uses predictive information from prior heartbeats that results in a deflation time earlier than that of R wave deflation.

23. The apparatus of claim 13, wherein the processing unit calculates values of T2-T1 for periods of 20 heartbeats, and selects a trigger mode based on whether T2-T1 is greater than, less than, or equal to the threshold time for each of three consecutive 20 beat periods.

24. The apparatus of claim 13, wherein the processing unit determines the number of times deflation occurs on the R wave during a deflation timing evaluation period; and if the number of times deflation occurs on the R wave exceeds a threshold value, the processing unit selects a mode of deflation that uses information from prior heartbeats to predict a deflation trigger that targets a percentage of volume to be removed from the IAB prior to the next systolic upstroke.

25. The apparatus of claim 24, wherein the threshold value is 14 occurrences of deflation on the R wave during a period of 20 heartbeats.

26. The apparatus of claim 23, wherein the processing unit selects a mode of deflation of the IAB that is triggered by the R wave of the ECG if during a deflation timing evaluation period, T2-T1 is less than 76 msec and if the number of occurrences of deflation on the R wave is less than 15 per 20 heartbeats.

27. The apparatus of claim 13, wherein the apparatus further comprises an output from the processing unit that selects the mode of deflation timing used to trigger deflation of the IAB.

28. An intra-aortic balloon pump console system comprising the apparatus of claim 13.

* * * * *